United States Patent [19]

Fischer et al.

[11] Patent Number: 4,900,682

[45] Date of Patent: Feb. 13, 1990

[54] METHOD AND REAGENT FOR THE DETERMINATION OF PERACIDS

[75] Inventors: Wolfgang Fischer, Darmstadt; Edda Arlt, Nieder-Ramstadt; Barbara Brabander, Ober-Ramstadt, all of Fed. Rep. of Germany

[73] Assignee: Merck Patent Gesellschaft mit Beschrankter Haftung, Darmstadt, Fed. Rep. of Germany

[21] Appl. No.: 285,700

[22] Filed: Dec. 16, 1988

[30] Foreign Application Priority Data

Dec. 19, 1987 [DE] Fed. Rep. of Germany ....... 3743224

[51] Int. Cl.$^4$ ............................................. G01N 33/00
[52] U.S. Cl. .................................... 436/129; 436/135; 436/164
[58] Field of Search ................. 436/129, 127, 825, 66, 436/100, 101, 102, 135, 164

[56] References Cited

U.S. PATENT DOCUMENTS

Re. 28,575  10/1975  Bauer ..................................... 436/66
4,143,080    3/1979  Harders et al. ....................... 436/66
4,556,640   12/1985  Gantzer ................................ 436/66
4,772,561    9/1988  Genshaw ............................. 422/56

OTHER PUBLICATIONS

Shapilov, O. D., "Photometric Determination of Peroxy-acids in the presence of Hydrogen Peroxides", Chemical Abstract, vol. 18, Jun. 1970, Abstr. 4100.
Frew et al., J. E., "Spectrophotometric Determination of Hydrogen Peroxide and Organic Hydroperoxides at Low Concentrations in Aqueous Solution", Analytica Chemica Acta, 155, pp. 139–150, (1983).

Primary Examiner—Barry S. Richman
Assistant Examiner—Thalia P. Vassilatos
Attorney, Agent, or Firm—Millen, White & Zenalo

[57] ABSTRACT

The invention relates to a method and reagent for the determination of peracids. The method is characterized in that the sample solution is mixed with a chromogen, an iodide and, where appropriate, a buffer-containing reagent, and the color reaction is evaluated, e.g., visually or by spectrophotometry.

15 Claims, No Drawings

METHOD AND REAGENT FOR THE DETERMINATION OF PERACIDS

BACKGROUND OF THE INVENTION

The invention relates to a method and reagent for the determination of peracids, especially for the determination of peracetic acid in the presence of hydrogen peroxide.

Peracetic acid is now increasingly being used for the purposes of disinfection because the resulting reaction products are environmentally acceptable, i.e., acetic acid, water and oxygen. Since the disinfectant activity depends on the concentration of the peracids which decompose with time, repeated assays are important for checking the level of activity of the peracids.

The main problem with assays is that, in addition to acetic acid, aqueous peracetic acid solutions also contain hydrogen peroxide. In most cases, the latter shows similar reactions to peracetic acid so that a determination of the total content of peracetic acid and hydrogen peroxide is obtained by conventional assays, for example, in Anal. Chim. Acta 155, 139 (1983). This determination of the total is, however, not very informative because the disinfectant action derives primarily from the peracetic acid.

Chemical Abstract, vol. 18, 1970, Abstr. 4100, discloses a method for the photometric determination of peracids in the presence of hydrogen peroxide, which is based on the oxidation of m-phenylenediamine by organic peracids at 50°–55° C. and a pH of 2–3 within 30–40 minutes, whereas hydrogen peroxide does not have an oxidative action under these conditions. This method is, in the same way as those which consist of two titrations which have to be carried out successively with different reagents, very time-consuming and requires suitable laboratory equipment and trained laboratory staff.

SUMMARY OF THE INVENTION

An object of the invention is to provide a method and reagent with which it is possible to determine peracids in a straightforward manner even in the presence of other peroxides.

Upon further study of the specification and appended claims, further objects and advantages of this invention will become apparent to those skilled in the art.

These objects are, surprisingly, achieved by a method which is specific for peracids even in the presence of hydrogen peroxide and is straightforward to carry out wherein the color reagents and, if appropriate, buffers customary for the detection of peroxides are used but, at the same time, the oxygen-carrying catalyst (for example ammonium molybdate, peroxidase) is omitted and instead an iodide is added.

Under these conditions, hydrogen peroxide virtually does not react or reacts only after a very long delay, whereas the peracid reacts rapidly and evidently. Hence, a method of this type allows the determination of peracids even in the presence of hydrogen peroxide.

The invention relates to a method for the determination of peracids, which is characterized in that the sample solution is mixed with a chromogen, an iodide and, where appropriate, a buffer-containing reagent, and the color reaction is evaluated by spectrophotometry or visually.

The invention furthermore relates to a reagent for the determination of peracids, containing a chromogen, an iodide and, where appropriate, a buffer. The reagent is preferably in the form of an impregnated matrix. For the specific determination of peracetic acid in the presence of hydrogen peroxide, the matrix is preferably impregnated with a chromogen, an iodide and a buffer.

In principle, it is possible with the method according to the invention to determine all peracids, preferably peracetic acid, perpropionic acid, perbutyric acid, perbenzoic acid and derivatives thereof. In this connection, peracetic acid has particular importance because it is widely used as a disinfectant due to its bactericidal, fungicidal, sporicidal and virucidal action. Peracetic acid is particularly distinguished from other disinfectants by its short action time and its low use concentrations (0.01–0.2% by weight). However, relatively rapid hydrolysis to acetic acid and hydrogen peroxide takes place particularly in dilute solutions, so that the content of peracetic acid, from which the disinfectant activity primarily derives, decreases continuously.

Chromogens which can be used are all the chromogens which are known from the literature to be able to be oxidized in the presence of peroxides. Suitable examples include but are not limited to aromatic amines such as o-toluidine, o- and p-phenylenediamine, 4,4'-diaminodiphenylamine, 2,7-diaminofluorine, benzidine and benzidine derivatives such as o-tolidine, o-dianisidine or tetramethylbenzidine, phenols such as o-cresol, guaiacol, pyrogallol, hydroquinone or 4-chloro-1-naphthol, leuko dyestuffs such as leukomalachite green or reduced 2,6-dichlorophenol-indophenol, preferably tetramethylbenzidine.

However, besides these it is also possible to use the known reagent combinations which can be oxidized by peroxides in the presence of a catalyst to give dyestuffs, examples thereof including but not being limited to 4-aminoantipyrine with phenol or N,N-dialkylaniline or else 3-methyl-2-benzothiazolinone hydrazone with N,N-dialkylanilines.

The chromogens should be present in stoichiometric excess. Unchanged chromogen ought to be still present even at the highest peracid concentrations to be detected.

An essential factor for the determination of peracids according to the invention is the addition of a source of iodide in place of an oxygen-carrying catalyst as is otherwise necessary for the conventional peroxide detections. Without iodide, the test according to the invention would be completely unsuitable as a rapid test in particular, because heating to above 50° C. for more than half an hour would be necessary before the test could be evaluated. Suitable iodides include but are not limited to the alkali metal iodides and ammonium iodide, preferably potassium iodide.

The iodide concentration can be very low, for example of the order of one tenth of the chromogen concentration. Although the iodide is initially consumed in the redox reaction which takes place, it is then formed anew.

In order to allow the reaction to take place at an optimum pH range, the reagent also contains, where appropriate, buffer substances. These are unnecessary if the color reaction is evaluated by spectrophotometry. However, if the peracids are determined with the aid of a matrix impregnated with the required reagents, the presence of buffer substances are advantageous.

Suitable buffers are those which maintain a pH range of about 3 to 6 and do not interfere with the detection reaction. The buffer concentration to be used depends on the pH of the sample solution and on any free acid or base which is present therein. Suitable buffers are described in the literature, examples thereof including but not limited to: the conventional salts such as phosphates, citrates, borates, etc., preferably phosphate buffer.

The reagent according to the invention can be used both as solution and in the form of absorbent matrices impregnated therewith, preferably in the form of test sticks.

Absorbent matrices which can be used are all those which are customarily employed for such rapid tests. The most widely used is filter paper, but it is also possible to use other absorbent cellulose or synthetic products. The absorbent carriers, preferably filter paper, are impregnated in a manner known per se with impregnation solutions which contain the reagents required for the determination of the peracid. The impregnated and dried papers can be processed into square or rectangular zones which in turn can be fixed in a known manner by adhesive or sealing onto synthetic films or strips of paper or metal.

The absorbent carriers can also, before impregnation, be applied in the form of strips to a synthetic tape and, after impregnation, cut into handy sticks at right angles to the direction of the strips.

To carry out the test, the absorbent carrier is immersed for about 1 to 3 seconds in the solution to be investigated and, after about 15 seconds, the color is compared or correlated with a color scale and the corresponding content of peracid is read off.

For a precise quantitative determination, a reagent solution is added to the sample to be investigated, which is in a cuvette, mixed and, after about 2 minutes, measured in a spectrophotometer. In case of a chromogen concentration of 0.5% the concentration of the iodide should be in the range of 0.001 to 0.1%. The quantitative determination according to the invention can be performed within about 5 to 150 seconds at about 10° to 25° C.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, cited above and below, and of corresponding application German P. No. 37 43 224.9, filed Dec. 19, 1987 (the priority document), are hereby incorporated by reference.

EXAMPLES

EXAMPLE 1

Determination of peracetic acid with a test stick

A filter paper (Schleicher & Schüll 2992) is impregnated successively with the following reagent solutions and dried with hot air after each impregnation:
Solution 1:
1: 125 g of sodium dihydrogen phosphate
125 g of disodium hydrogen phosphate
0.5 g of potassium iodide in 1 l of water
Solution 2: 5 g of tetramethylbenzidine in 1 l of ethanol.

To establish the detection range, a 5% peracetic acid solution is diluted to obtain solutions in the concentration range from 0.001 to 0.2%. The exact peracetic acid concentrations in the individual dilutions are established by the titration method described in the literature.

Test sticks prepared by fixing the impregnated filter paper to white films with adhesive are immersed in these solutions. The intensity of the resulting blue colorations varies as a function of the concentration. Hydrogen peroxide solutions do not react.

The experiments show that the following concentrations of peracetic acid generate different colors and thus can be determined with the aid of an appropriate color scale: 0, 5, 10, 30, 60, 100, 500 and 2000 ppm.

EXAMPLE 2

10 ml of each peracetic acid solution in the concentration range from 0.0005 to 0.01% are mixed with 1 ml of a solution of 0.3 g of 4-chloro-1-naphthol and 0.03 g of sodium iodide in 100 ml of 1% acetic acid. The resulting solutions are placed in a 10 mm cuvette and, after 2 minutes, the extinction at 528 nm is determined in a spectrophotometer.

The dependence of the extinction on the concentration of peracetic acid is plotted in the form of a calibration graph. This calibration graph can be used to determine the peracetic acid content in unknown solutions.

EXAMPLE 3

A test stick prepared according to Example 1 is used in connection with pure hydrogen peroxide solutions in the concentration range between 0.005 and 0.5%. The test sticks are immersed in these solutions with the result that within 30 seconds no color reaction occurs.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the determination of the concentration of a peracid in a sample solution, comprising mixing said sample solution with reagent containing a chromogen and an iodide and comparing the resultant color of the mixture with a standard to determine the amount of peracid in the sample solution.

2. A method according to claim 1, wherein said reagent further contains a buffer to effect a pH of 3–6.

3. A method according to claim 1, wherein the color of said resultant mixture is measured by spectrophotometry.

4. A method according to claim 1, wherein said sample solution contains hydrogen peroxide.

5. A method according to claim 1, wherein said mixture does not contain an oxygen-containing catalyst.

6. A method according to claim 1, wherein said peracid is peracetic acid, perpropionic acid, perbutyric acid, perbenzoic acids or mixtures thereof.

7. A method according to claim 6, wherein said peracid is peracetic acid.

8. A method according to claim 1, wherein said iodide is an alkali metal iodide, ammonium iodide or mixtures thereof.

9. A method according to claim 1, wherein said iodide is potassium iodide.

10. A method according to claim 2, wherein said reagent is in the form of an impregnated matrix.

11. A method according to claim 10, wherein said matrix is impregnated with tetramethylbenzidine, potassium iodide and a phosphate buffer.

12. A method according to claim 1, wherein said chromogen is o-toluidine, o-phenylene-diamine, p-phenylene-diamine, 4,4'-diaminodiphenylamine, 2,7-diaminofluorine, benzidine., o-tolidihe , o-dianisidine, tetramethylbenzidine, o-cresol, guaiacol, pyrogallol, hydroquinone, 4-chloro-1-naphthol, leukomalachite green or reduced 2,6-dichlorophenol-indophenol.

13. A method according to claim 1, wherein said chromogen is present in said reagent in an amount in excess of the peracid concentration in said sample solution.

14. A method according to claim 1, wherein the relative concentration of chromogen to iodide is 1:0.002 to 1:0.2

15. A method according to claim 1 conducted at about 10°-25° C. within about 5 to 150 seconds.

* * * * *